US00PP08492P

United States Patent [19]

Laver

[11] Patent Number: Plant 8,492

[45] Date of Patent: Dec. 14, 1993

[54] MINIATURE ROSE PLANT NAMED 'LAVPET'

[75] Inventor: Keith Laver, Ontario, Canada

[73] Assignee: The Conard-Pyle Company, West Grove, Pa.

[21] Appl. No.: 963,385

[22] Filed: Oct. 19, 1992

[51] Int. Cl.[5] ..... A01H 5/00
[52] U.S. Cl. ..... Plt./8.2
[58] Field of Search ..... Plt./8.2, 24

*Primary Examiner*—Howard J. Locker
*Attorney, Agent, or Firm*—Burns, Doane, Swecker & Mathis

[57] ABSTRACT

A new and distinct variety of rose plant of the Miniature Class is provided which abundantly forms in uniform clusters attractive long-lasting double blossoms having an exhibition-type form of a very stable chrome yellow coloration. The plant is very bushy and compact, and forms light to medium green vegetation. The blossoms are very slightly fragrant. The plant is well adapted to forcing while grown in small containers, and is particularly well suited for use as a flowering pot plant when grown indoors or outdoors. Additionally, the plant is not particularly affected by cryptogamic diseases.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) was the showbound variety (nonpatented in the United States). The male parent (i.e., the pollen parent) of the new variety was the product of the pollination of the Party Girl variety(U.S. Plant Pat. No. 4,598) by the JUNE LAVER variety (nonpatented in the United States). The parentage of the new variety can be summarized as follows:

Showbound × (Party Girl × June Laver).

The seeds resulting from the above pollination were sown and small plants were obtained which were physically and biologically different from each other. Selective study resulted in the identification of a single plant of the new variety.

It was found that the new variety of miniature rose plant of the present invention possesses the following combination of characteristics:

(a) forms in abundance in uniform clusters attractive double long-lasting blossoms having an exhibition-type form which are of a very stable chrome yellow coloration,
(b) forms dark green foliage,
(c) exhibits a very bushy growth habit,
(d) is particularly suited for use as a flowering pot plant for indoor or outdoor decoration,
(e) is well adapted to forcing when grown in small containers, and
(f) is not particularly affected by cryptogamic diseases.

The new variety well meets the needs of the horticultural industry. It serves well as attractive ornamentation as a flowering pot plant when grown indoors or outdoors. The flowering is very uniform and the blossoms are relatively stable in coloration upon the passage of time.

The new variety has been found to undergo asexual propagation at West Grove, Pa., U.S.A., by a number of routes, including budding, grafting, cuttage, etc. The characteristics of the new variety have been found to be strictly transmissible by such asexual propagation from one generation to another.

The new variety has been named the Lavpet variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age were observed during September while growing in containers on their own roots in the greenhouse at West Grove, Pa., U.S.A.

At the left (top) are shown specimens of four buds which illustrate the opening progression from left to right. At the left (middle) are shown specimens of a young stem and a flowering shoot. At the left (bottom) are shown specimens of two main branches. At the middle are illustrated specimens of blooms in progressive stages of opening with the newly opened blooms being shown at the top and the fully open blooms being shown at the bottom wherein the obverse is shown at the left and the reverse is shown at the right. At the right are illustrated specimens of leaves with three, five, and seven leaflets with the upper surfaces being shown at the right and the under surfaces being shown at the left.

DETAILED DESCRIPTION

The chart used in the identification of the colors is that of The Royal Horticultural Society (R.H.S. Colour Chart). The terminology which precedes reference to the chart has been added to indicate the corresponding in common terms The description is based on one year old specimens of the variety which where observed during September while growing in containers on their own roots in the greenhouse at West Grove, Pa., U.S.A.

Class: Miniature.
Plant:

Height.—Approximately 12 to 15 inches on average when grown in one-gallon containers.

*Habit.*—Very compact and very bushy.

Branches:

Color.—Young stems: light green, Yellow-Green Group 144C. Adult wood: Lettuce Green, Yellow-Green Group 144A.

*Thorns.*—Size: long. Quantity: below average. Color: yellowish and sometimes stained with reddish coloration.

Leaves:

Petioles.—Upper surface: yellowish-green and stained with light reddish coloration on young foliage and medium green on mature foliage with glandular edges. Under surface: light green, and bear a few prickles which sometimes develop into true thorns.

*Stipules.*—Adnate, pectinate, wide and linear.

Leaflets.—Number: 3, 5 (most often), and 7. Shape: spearlike. Serration: single and regular. Texture: consistent. General appearance: dense, bright foliage. Color (young foliage): Upper surface: lettuce Green, Yellow-Green Group 144A, and edged with reddish coloration on very young stems. Under surface: light green, Green Group 138B. Color (adult foliage): upper surface: dark green, Green Group 137A. under surface: medium green, Green Group 138B.

Inflorescence:

*Number of flowers.*—Approximately 1 to 5 per stem, and usually approximately 3 per stem.

*Peduncle.*—Rigid, yellowish green in coloration, fairly straight, bears numerous tiny prickles, its length is approximately 1.5 to 2 cm. on average.

*Sepals.*—Upper surface: tomentose and greenish in coloration. Under surface: light green in coloration, bear tiny glandular acicules near the edges, and the outer sepals usually end with leaf-like appendices.

*Buds.*—Shape: ovoid. Length: approximately 1 cm. on average immediately prior to opening. Size: small. Color upon opening: Upper surface: Chartreuse Green, Green-Yellow Group 1B. Under surface: Chartreuse Green, Yellow-Green Group 154B.

Flower.—Form: cup-like, double. Diameter: approximately 3 to 3.5 cm. on average when fully open. Color (when opening begins): Upper surface: Chrome Yellow, Yellow-Orange Group 15C, and turning to Chartreuse Green, Green-Yellow Group 1C, near the point of attachment. Under surface: Chrome Yellow, Yellow-Orange Group 15C, and turning to Chartreuse Green, Green-Yellow Group 1C, near the point of attachment. Color (when blooming): Upper surface: Chrome Yellow, Yellow-Orange Group 15C, with a greenish claw. Under surface: Chrome Yellow, Yellow-Orange Group 15C, with a greenish claw. Color (at end of blooming): Upper surface: light Chrome Yellow, Yellow-Orange Group 15C, and turning to Yellow-Orange Group 15D. At this stage the pistils and stamens are clearly visible at the center of the bloom. Under surface: light Chrome Yellow, Yellow-Orange Group 15C, and turning to Yellow-Orange Group 15D. At this stage the pistils and stamens are clearly visible at the center of the bloom. Fragrance: slight. Lasting quality: long on the plant. Petal number; approximately 22 to 25 on average. Petal shape: rounded. Petal Texture: firm. Petal drop: very good. Anthers: strawlike, fairly regular in height, and located at substantially the same height as the stigmas. Stamen number: approximately 52 to 55 on average. Filaments: bright yellow, free standing, fairly regular in height, and uniformly located around the receptacle. Pistil number: approximately 20 to 22 on average. Stigmas: normal, fuchsia colored. Styles: twisted, of irregular heights, and whitish with a fuchsia cast near the top. Receptacle: narrow and funnel-shaped.

Development:

*Vegetation.*—Vigorous and very regular.

*Blooming.*—Abundant in flushes.

Aptitude to bear fruits.—None.

*Resistance to diseases.*—Good.

I claim:

1. A new and distinct variety of miniature rose plant characterized by the following combination of characteristics:

(a) forms in abundance in uniform clusters attractive double long-lasting blossoms having an exhibition-type form which are of a very stable chrome yellow coloration, (b) forms dark green foliage, (c) exhibits a very bushy growth habit, (d) is particularly suited for use as a flowering pot plant for indoor or outdoor decoration, (e) is well adapted to forcing when grown in small containers, and (f) is not particularly affected by cryptogamic diseases;

substantially as herein shown and described.

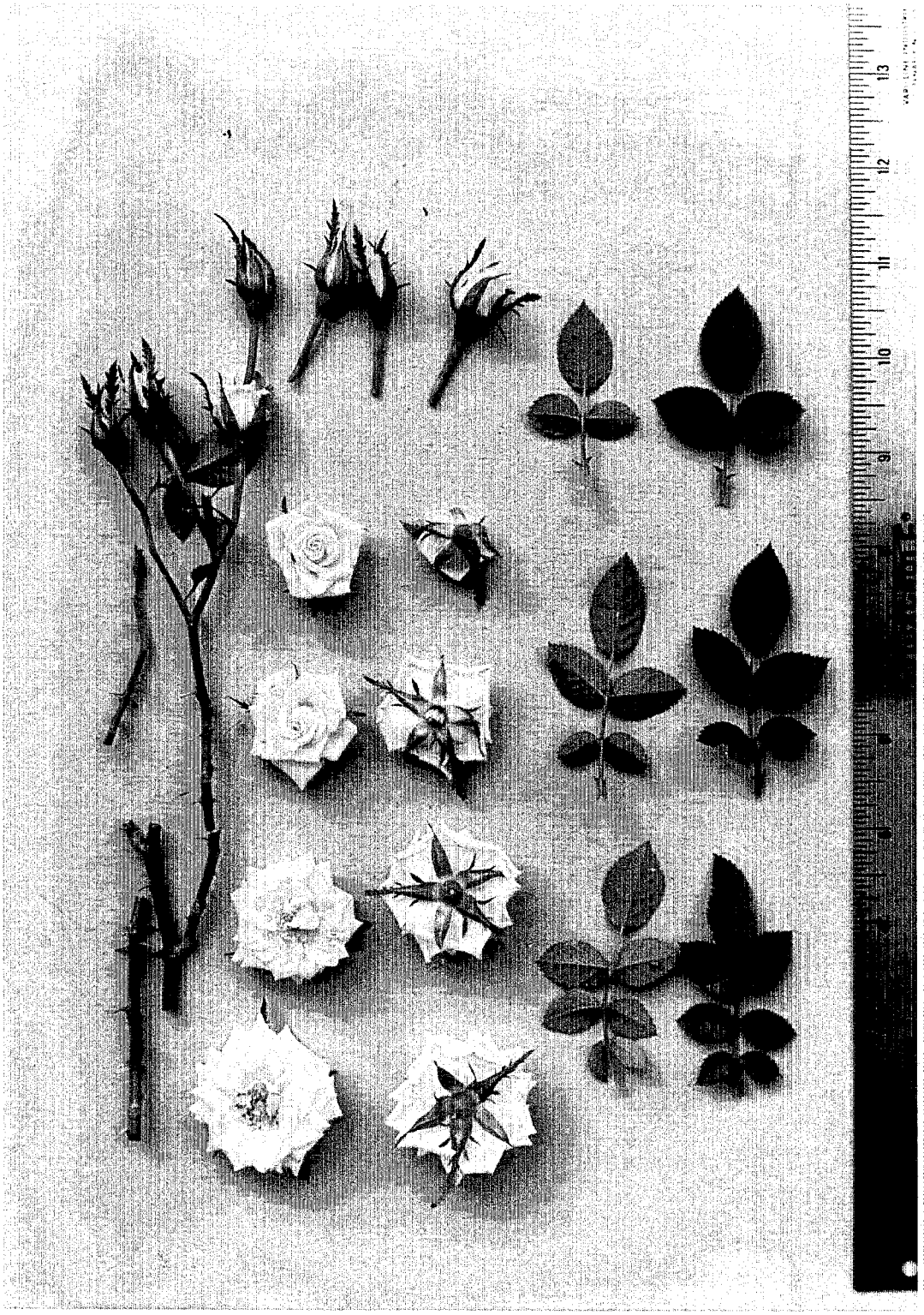

* * * * *